United States Patent [19]

Brown

[11] Patent Number: 4,953,902
[45] Date of Patent: Sep. 4, 1990

[54] DEVICE FOR ADHESIVELY HOLDING SMALL OBJECTS

[76] Inventor: Martin A. Brown, 11604 Manitou Dr., Fountain Hills, Ariz. 85268

[21] Appl. No.: 247,403

[22] Filed: Sep. 21, 1988

[51] Int. Cl.⁵ .......................... A61C 3/00; B25J 15/00
[52] U.S. Cl. ...................................... 294/1.1; 433/141
[58] Field of Search .......................... 294/1.1, 1.2, 19.1, 294/64.1; 15/104 R, 104 A, 104.94; 221/210; 271/33; 401/101, 103, 115, 117, 138, 140; 433/89, 90, 141, 163, 229

[56] References Cited

U.S. PATENT DOCUMENTS

| | | | |
|---|---|---|---|
| 517,295 | 3/1894 | Pulling | 294/1.1 X |
| 939,476 | 11/1909 | Copp | 294/1.1 X |
| 2,603,871 | 7/1952 | Call | 433/90 |
| 3,026,616 | 3/1962 | Clark | 433/90 |
| 3,091,860 | 6/1963 | Baughan | 433/90 |
| 3,468,031 | 9/1969 | Mumaw | 433/141 X |
| 3,721,006 | 3/1973 | Malmin | 433/229 |
| 3,797,875 | 3/1974 | den Hamer | 294/1.1 |
| 3,974,539 | 8/1976 | Barouh et al. | 294/1.1 X |
| 4,073,530 | 2/1978 | Seidler | 294/1.1 X |
| 4,600,227 | 7/1986 | Ennis et al. | 294/1.1 |
| 4,746,292 | 5/1988 | Johnson | 433/141 |
| 4,822,278 | 4/1989 | Oliva et al. | 433/141 X |
| 4,834,654 | 5/1989 | Nussbaum | 294/1.1 X |

*Primary Examiner*—Johnny D. Cherry
*Attorney, Agent, or Firm*—Harry M. Weiss

[57] ABSTRACT

A porcelain veneer placement holder is provided for picking up a small porcelain veneer piece and placing it on a surface of a tooth. The holder includes an elongated handle having an end portion, a plunger fixedly connected to and cantilevered from the end portion, a hollow cylinder slidably mounted on the plunger and forming an open-ended variable-volume chamber containing an adhesive material. The adhesive material is extruded for making a small deposit at the top of the cylinder. The handle end portion has a peripheral wall cantilevered therefrom and is coaxial with the plunger along a plunger axis. The peripheral wall and the plunger form a cylindrical cavity therebetween, which receives the cylinder. The end portion and the plunger axis are disposed at an angle to the handle.

6 Claims, 1 Drawing Sheet

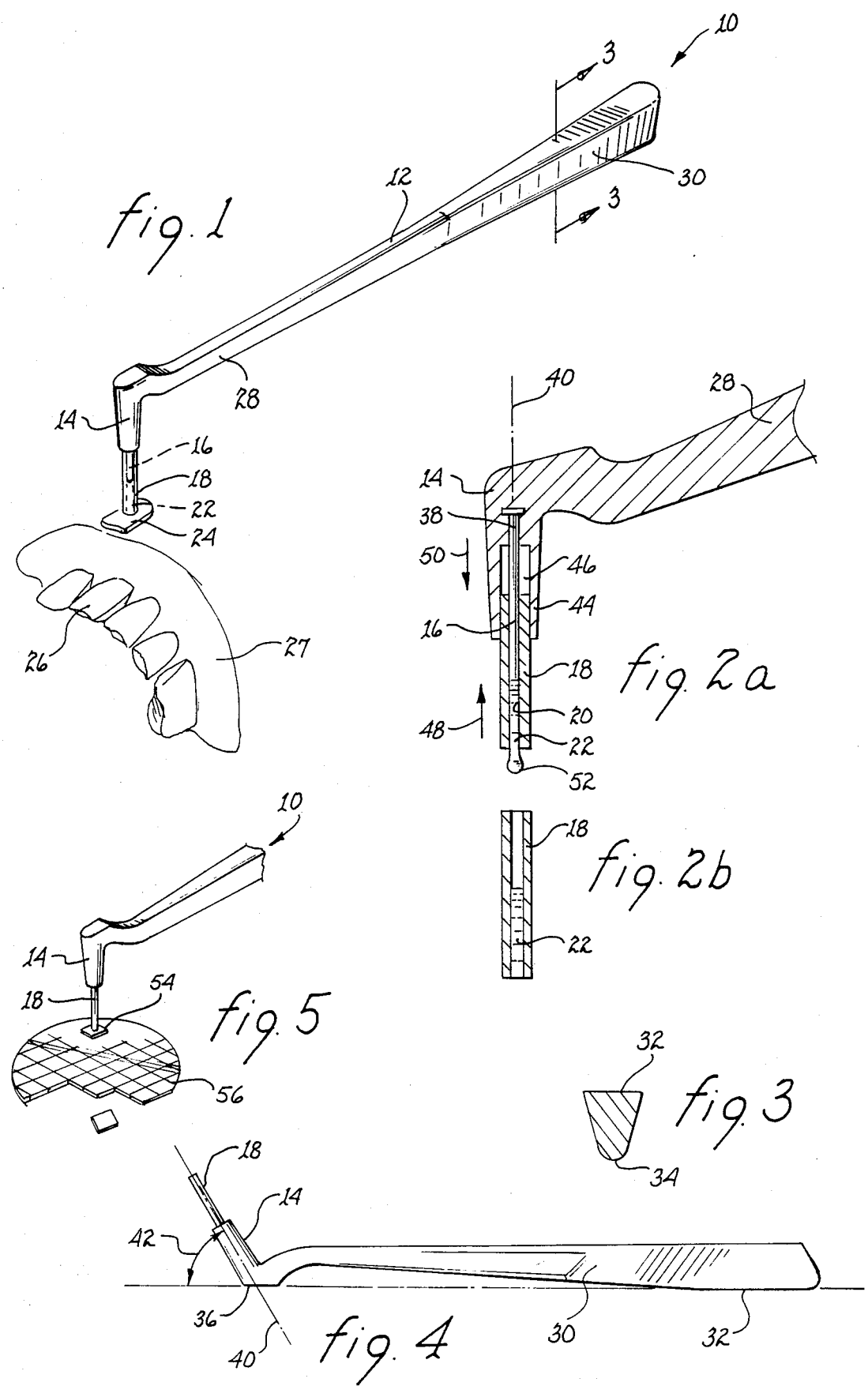

DEVICE FOR ADHESIVELY HOLDING SMALL OBJECTS

BACKGROUND OF THE INVENTION

1. Field of the Invention

The invention generally relates to a placement holder and process, and, in particular, the invention relates to a porcelain veneer placement holder and process having an elongate handle and a hollow cylinder containing adhesive and being mounted on an end of the handle.

2. Description of the Related Art

The prior art placement holder includes a finger grip stem portion and a suction cup mounted on an end of the stem portion.

One problem with the prior art placement holder is that the porcelain veneer separates from the placement holder due to a loss of suction.

SUMMARY OF THE INVENTION

According to the present invention, a porcelain veneer placement holder is provided. This placement holder comprises an elongate handle having an end portion, a fixed plunger fixedly connected to the end portion, a displaceable hollow cylinder slidably mounted on the cylinder and forming therewith an open ended variable volume chamber, and adhesive material disposed in the chamber for extrusion from the cylinder.

By using the plunger and hollow cylinder and adhesive material, the problem of separation of the porcelain veneer from the placement holder is avoided.

The foregoing and other objects, features and advantages will be apparent from the following description of the preferred embodiment of the invention as illustrated in the accompanying drawings.

BRIEF DESCRIPTION OF THE DRAWINGS

FIG. 1 is a perspective view of a placement holder according to the invention;

FIG. 2a is an enlarged section view of a portion of FIG. 1;

FIG. 2b is a section view of one portion of FIG. 2a;

FIG. 3 is a section view as taken along the line 3—3 of FIG. 1;

FIG. 4 is an elevation view of the placement holder of FIG. 1 at rest; and

FIG. 5 is a partial perspective view of the placement holder of FIG. 1 in a second application of use.

DESCRIPTION OF THE PREFERRED EMBODIMENT

As shown in FIGS. 1 and 3, a placement holder 10 is provided in an application of dental repair. Holder 10 has an elongate handle 12 which has an end portion 14. Holder 10 has a plunger 16, which is fixedly connected to end portion 14, and a hollow cylinder 18, which is slidably mounted on plunger 16 and which is displaceable relative to plunger 16. Plunger 16 and cylinder 18 form a variable volume chamber 20 which contains an adhesive material 22. Holder 10 is used to hold a small porcelain veneer or member 24 which is to be attached to a tooth 26 in mouth 27 using an attaching material (not shown).

Handle 12 has a narrow middle portion 28, which is fixedly connected to end portion 14. Handle 12 also has an enlarged opposite end portion 30.

As shown in FIG. 3, enlarged portion 30 has a flat resting surface 32 and has an opposite rounded surface 34.

In FIG. 4, end portion 14 has a flat resting surface 36, which is coplanar with resting surface 32. This permits the handle 12 to be placed in a position so that the object 24 is in an upward position away from contamination prior to placement.

In FIG. 2a, plunger 16 has an imbedded portion 38, which is fixedly connected to end portion 14 and which is cantilevered from end portion 14.

In FIG. 4, plunger 16 has an axis 40 which is at an angle 42 to surface 36. Angle 42 is about sixty degrees in size.

In FIG. 2a, end portion 14 has a peripheral wall 44. Wall 44 and plunger 16 form a cylindrical cavity 46 therebetween.

Cylinder 18, which is a capillary tube, is received in cavity 46. Cylinder 18 and plunger 16 form the variable volume chamber 20 which contains adhesive 22.

In FIG. 2a, plunger 16 extrudes a small adhesive portion 52 when a force in the upward direction 48 is applied to cylinder 18. End portion 14 also applies a force in the downward direction 50 through plunger 16 to adhesive 22. Adhesive portion 52 is just outside of chamber 20 adjacent to the end of cylinder 18 for holding the porcelain veneer or piece 24.

In FIG. 2b, adhesive 22 can be inserted into chamber 20 before or after, cylinder 18 is slidably mounted on plunger 16. Cylinder is can be made as a throw away product, as desired. A capillary action occurs in the process of partially filling cylinder 18 with adhesive 22.

A selective clearance is provided between the outside diameter of cylinder 18 and the inside diameter of wall 44. Another selective clearance is provided between the outside diameter of plunger 16 and the inside diameter of cylinder 18.

In operation, a veneer piece, for example, piece 24, can also be applied to the outer surface of a tooth 26, as required.

In use, holder 10 is generally used to pick up relatively small objects like veneer piece 24. Holder 10 is primarily used to pick up a veneer piece 24 to place it on a tooth 26. Veneer piece 24 can be placed on the front side of a tooth. The veneer piece 24 is attached to tooth 26 using an attaching material (not shown) such as an adhesive. One purpose of holder 10 is to be able to pick up a small object without touching it with the fingers and to place the small object where desired. With the device of this invention, objects that are to be picked up will have greater visibility to the person picking up the object for proper orientation and placement. The placed object will now have greater ease of accessibility to other instrumentation. The holder 10 can be used for placement of objects for either front or back teeth.

A key feature of holder 10 is the use of adhesive material 22, which is inserted in a bottom end portion of cylinder 18, so that when cylinder moves upwardly by applying a downward pressure 50 on the handle 12, plunger 16 causes the small adhesive portion 52, or a like sticky material, to be extruded from the tip of cylinder 18 onto a small object, like veneer piece 24, to be lifted or moved.

FIG. 5 shows another application of holder 10. Holder 10 holds a small semiconductor chip 54, which is to be lifted and moved and placed on a printed circuit board (not shown). Chip 54 is picked up from a chip array 56.

While the invention has been described in its preferred embodiment, it is to be understood that the words which have been used are words of description rather than limitation and that changes may be made within the purview of the appended claims without departing from the true scope and spirit of the invention in its broader aspects.

I claim:

1. A placement holder for lifting small objects comprising, in combination:

adhesive material by which said small objects are lifted;

plunger means for releasing said adhesive material;

a hollow cylinder slidably mounted on said plunger means, said cylinder forming open-ended chamber means for containing said adhesive material; and handle means fixedly coupled to said plunger means for manipulating said placement holder, said handle means having a first end portion comprising a peripheral wall cantilevered therefrom coaxially with said plunger means forming a cylindrical cavity therebetween, with said cylinder slidably mounted within said cylindrical cavity, and second end portion.

2. The holder of claim 1 wherein said handle means is elongated in length.

3. The holder of claim 1 wherein said first and second end portions each having substantially flat portion means for permitting said holder to be laid upside down.

4. The holder of claim 3 wherein said second end portion further comprises a rounded surface extending downward from said flat portion means of said second end portion.

5. The holder of claim 3, wherein said handle means has a relatively narrow middle portion, and said second end portion is a relatively enlarged portion.

6. The holder of claim 1 wherein said plunger means is disposed at an angle of approximately sixty degrees from said handle means.

* * * * *